(12) United States Patent
Chakrabartty et al.

(10) Patent No.: US 11,464,487 B2
(45) Date of Patent: Oct. 11, 2022

(54) SYSTEMS AND METHODS FOR DETECTING EMBEDDED TARGET ELEMENTS USING SIGNAL INTERFERENCE

(71) Applicants: Shantanu Chakrabartty, St. Louis, MO (US); Yarub Alazzawi, St. Louis, MO (US); Srikanth Signamaneni, St. Louis, MO (US); Keng-Ku Liu, Richmond Heights, MO (US); Mingquan Yuan, St. Louis, MO (US)

(72) Inventors: Shantanu Chakrabartty, St. Louis, MO (US); Yarub Alazzawi, St. Louis, MO (US); Srikanth Signamaneni, St. Louis, MO (US); Keng-Ku Liu, Richmond Heights, MO (US); Mingquan Yuan, St. Louis, MO (US)

(73) Assignee: Washington University, St. Louis, MO (US)

(*) Notice: Subject to any disclaimer, the term of this patent is extended or adjusted under 35 U.S.C. 154(b) by 1140 days.

(21) Appl. No.: 16/023,761

(22) Filed: Jun. 29, 2018

(65) Prior Publication Data

US 2019/0000419 A1    Jan. 3, 2019

Related U.S. Application Data

(60) Provisional application No. 62/527,563, filed on Jun. 30, 2017.

(51) Int. Cl.
*A61B 8/00* (2006.01)
*H01L 41/113* (2006.01)
(Continued)

(52) U.S. Cl.
CPC .......... *A61B 8/4483* (2013.01); *G01N 29/022* (2013.01); *G01N 29/036* (2013.01);
(Continued)

(58) Field of Classification Search
CPC .......... A61B 8/4483; G01N 2291/014; G01N 2291/0255; G01N 2291/0256;
(Continued)

(56) References Cited

U.S. PATENT DOCUMENTS 5,212,988 A * 5/1993 White ................ G01N 29/2437
73/602
5,306,644 A * 4/1994 Myerholtz ........... G01N 29/022
73/61.49

(Continued)

FOREIGN PATENT DOCUMENTS

WO      2002075261 A2    9/2002

OTHER PUBLICATIONS

Saad et al, Quartz Crystal Microbalance for Bacteria Application Review, Quartz Crystal Microbalance for Bacteria Application Review (Year: 2014).*

(Continued)

*Primary Examiner* — David L Singer
(74) *Attorney, Agent, or Firm* — Armstrong Teasdale LLP

(57) ABSTRACT

A sensor system includes a sensor module that is embedded in a target environment and a signal system. The sensor module includes an active sensor of a first type that detects a target element in the target environment and a reference sensor of the first type that prevents detection of target elements by the reference sensor. The active sensor and the reference sensor receive an ultrasonic signal and respectively generate a first response signal and a second response signal. The first response signal is at least partially as a function of the detected target element. The signal system includes an ultrasonic transducer that generates the ultrasonic signal and receives the first and second response signals, and a controller communicatively coupled to the ultrasonic transducer. The controller identifies the detected (Continued)

target element based at least partially on the first and second response signals.

**20 Claims, 10 Drawing Sheets
(8 of 10 Drawing Sheet(s) Filed in Color)**

(51) Int. Cl.
| | | |
|---|---|---|
| *G01N 29/24* | (2006.01) | |
| *G01N 29/036* | (2006.01) | |
| *G01N 29/02* | (2006.01) | |
| *G01N 29/44* | (2006.01) | |
| *G01N 29/30* | (2006.01) | |

(52) U.S. Cl.
CPC ......... *G01N 29/2437* (2013.01); *G01N 29/30* (2013.01); *G01N 29/4436* (2013.01); *H01L 41/1132* (2013.01); *G01N 2291/014* (2013.01); *G01N 2291/0255* (2013.01); *G01N 2291/0256* (2013.01); *G01N 2291/02809* (2013.01)

(58) Field of Classification Search
CPC . G01N 2291/02809; G01N 2291/0423; G01N 29/022; G01N 29/036; G01N 29/2437; G01N 29/30; G01N 29/4436; H01L 41/1132
See application file for complete search history.

(56) References Cited

U.S. PATENT DOCUMENTS

| | | | |
|---|---|---|---|
| 6,848,295 B2* | 2/2005 | Auner | G11B 5/855 |
| | | | 73/24.01 |
| 7,223,366 B2 | 5/2007 | Hauan et al. | |
| 7,771,987 B2 | 8/2010 | Edmonson et al. | |
| 8,346,482 B2 | 1/2013 | Fernandez | |
| 9,788,776 B1* | 10/2017 | Thompson | A61B 5/1455 |
| 2005/0022581 A1* | 2/2005 | Sunshine | H04Q 9/00 |
| | | | 73/31.05 |
| 2005/0028578 A1* | 2/2005 | Apostolos | G01N 29/022 |
| | | | 73/641 |
| 2005/0121999 A1* | 6/2005 | Edmonson | H03H 9/6406 |
| | | | 310/313 D |
| 2006/0049714 A1* | 3/2006 | Liu | G01S 13/755 |
| | | | 310/313 R |
| 2009/0280509 A1* | 11/2009 | Lee | G01N 33/6854 |
| | | | 435/7.1 |
| 2010/0087011 A1* | 4/2010 | Cooper | G01N 29/4418 |
| | | | 702/19 |
| 2015/0011428 A1* | 1/2015 | Cable | G01N 33/54393 |
| | | | 506/14 |
| 2015/0177196 A1* | 6/2015 | Sussner | G01N 29/2406 |
| | | | 73/24.04 |

OTHER PUBLICATIONS

Sangeetha et al, Readout Method for Pathogen Detection using Biosensor, ICICES2014—S.A.Engineering College, Chennai, Tamil Nadu, India (Year: 2014).*
Bhalla et al, Introduction to biosensors, Published by Portland Press Limited on behalf of the Biochemical Society, Essays in Biochemistry (2016) 60 1-8 (Year: 2016).*
Wan et al., Characterization of phage-coupled magnetoelastic microparticles for the detection of Bacillus anthracis Sterne spores, IEEE Sensors 2007 Conference (Year: 2007).*
Zhou et al, Interfacial Structures and Properties of Organic Materials for Biosensors: An Overview, Sensors 2012, 12, 15036-15062; doi: 10.3390/s121115036 (Year: 2012).*
Puiu et al, Enhanced Sensitive Love Wave Surface Acoustic Wave Sensor Designed for Immunoassay Formats, Sensors 2015, 15, 10511-10525; doi: 10.3390/s150510511 (Year: 2015).*
Scarano et al, SPR-Based Affinity Biosensors as Innovative Analytical Devices, Journal of Lightwave Technology, vol. 33, No. 16, Aug. 15, 2015 (Year: 2015).*

* cited by examiner

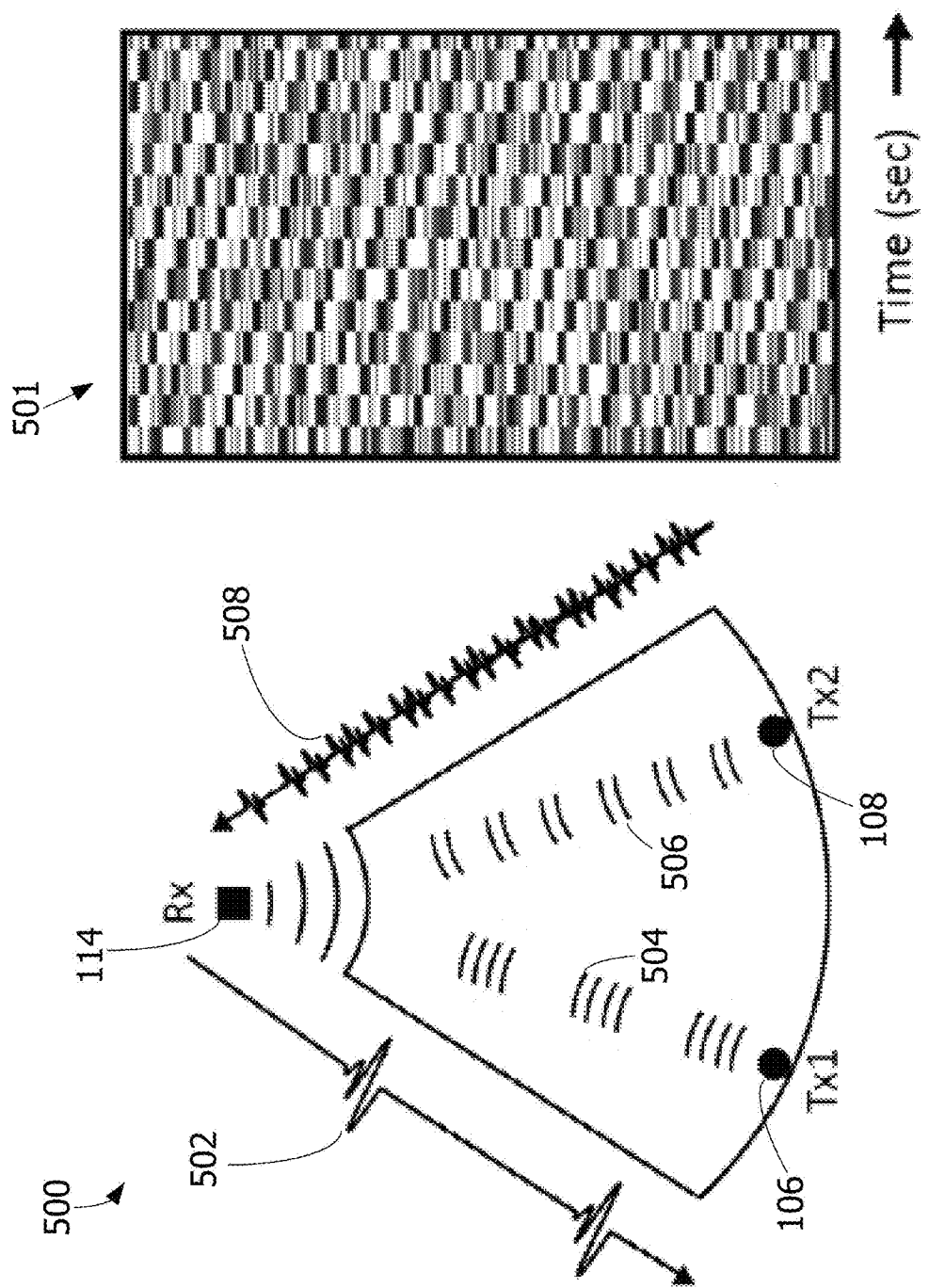

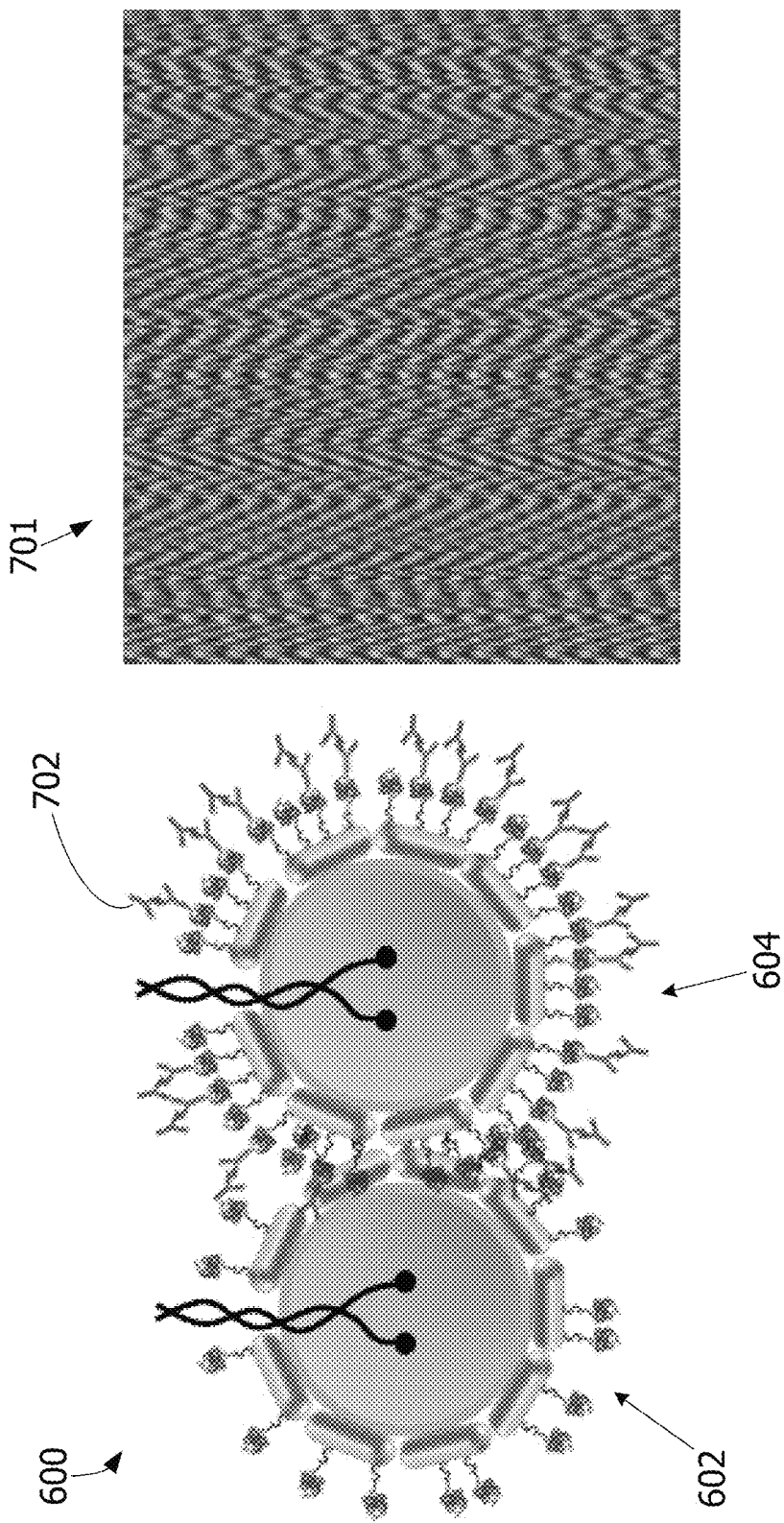

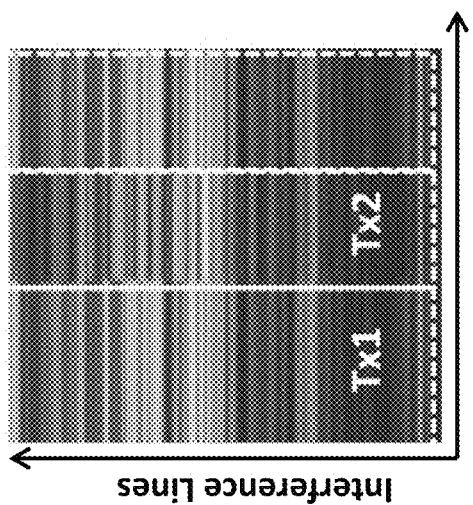
FIG. 10A
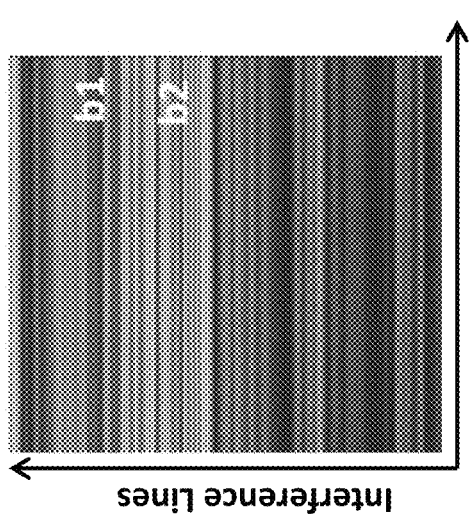
FIG. 10B
FIG. 10C
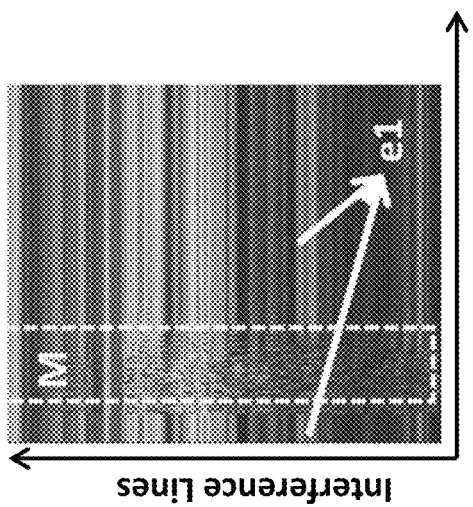
FIG. 10D
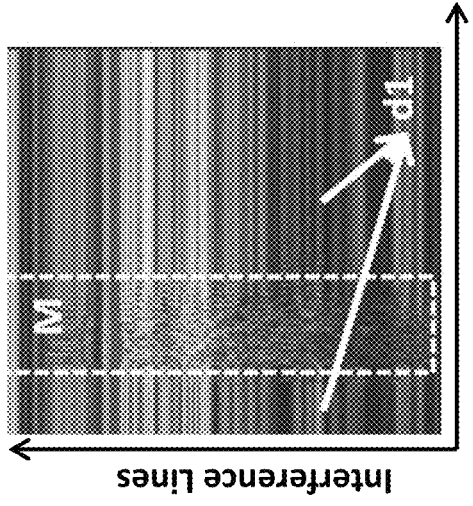
FIG. 10E

SYSTEMS AND METHODS FOR DETECTING EMBEDDED TARGET ELEMENTS USING SIGNAL INTERFERENCE

CROSS-REFERENCE TO RELATED APPLICATION

This application claims the benefit of U.S. Provisional Application Ser. No. 62/527,563, filed Jun. 30, 2017, entitled "SYSTEMS AND METHODS FOR DETECTING EMBEDDED TARGET ELEMENTS USING SIGNAL INTERFERENCE", which is hereby incorporated in its entirety herein.

BACKGROUND

The field of the disclosure relates generally to sensor systems, and more particularly to sensor systems including an active sensor for detecting target elements and a reference sensor for generating signal interference to identify the detected target elements.

Embedded sensors are used in various technology fields to collect sensor data from target environments that are difficult to monitor just using monitoring devices external to the target environment. For example, sensors may be implanted within a patient during a medical procedure to monitor a target environment after the procedure without requiring subsequent in vivo access to the environment. Typically, these sensors are communicatively coupled to a controller to store and process the sensor data. The controller may be communicatively coupled to the sensors using wired communication or wireless communication. Wired communication enables the sensors to be powered by the controller, but also requires the controller remain electrically coupled to the sensor to collect sensor data.

BRIEF DESCRIPTION

In one aspect, a sensor system includes a sensor module that is embedded in a target environment and a signal system. The sensor module includes an active sensor of a first type that detects a target element in the target environment and a reference sensor of the first type that prevents detection of target elements by the reference sensor. The active sensor and the reference sensor receive an ultrasonic signal and respectively generate a first response signal and a second response signal. The first response signal is at least partially as a function of the detected target element. The signal system includes an ultrasonic transducer that generates the ultrasonic signal and receives the first and second response signals, and a controller communicatively coupled to the ultrasonic transducer. The controller identifies the detected target element based at least partially on the first and second response signals.

In another aspect, a method for detecting a target element with a sensor system including a sensor module and a signal system is provided. The sensor module includes an active sensor of a first type and a reference sensor of the first type. The reference sensor prevents detection of target elements by the reference sensor. The method includes embedding the sensor module in a target environment including target elements, detecting a target element within the target environment using the active sensor, receiving an ultrasonic signal at the active sensor and the reference sensor from the signal system, generating a first response signal with the active sensor and a second response signal with the reference sensor, receiving the first and second response signals at the signal system, and identifying the detected target element based at least partially on the first and second response signals. The first response signal is generated at least partially as a function of the detected target element.

In yet another aspect, a sensor module is embedded in a target environment to detect target elements in the target environment. The sensor module includes an active sensor of a first type that detects a target element and a reference sensor of the first type that prevents detection of target elements by the reference sensor. The active sensor and the reference sensor receive an ultrasonic signal and respectively generate a first response signal and a second response signal. The first response signal varies at least partially as a function of the detected target element. The first and second response signals are transmitted to a signal system to identify the detected target element based at least partially on the first and second response signals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings described below illustrate various aspects of the disclosure.

FIG. 5A is a schematic diagram illustrating a transducer, a reference sensor, an active sensor, and associated signals forming interference patterns in accordance with an aspect of the disclosure;

FIG. 5B is a graph showing a representative measured signal interference pattern generated by the elements arranged as illustrated in FIG. 5A;

FIG. 7A is a diagram of the sensor module shown in FIG. 6A with target elements immobilized on the active sensor;

FIG. 7B is a graph showing a measured signal interference pattern generated using the sensor module illustrated in FIG. 7A;

FIG. 10A is a graph showing a measured interference pattern within a large-volume phantom device generated using the elements of the sensor module illustrated in FIG. 9A and FIG. 9B;

FIG. 10B is a graph showing a measured interference pattern within a small-volume phantom device generated using the elements of the sensor module illustrated in FIG. 9A and FIG. 9B;

FIG. 10C is a graph showing a measured interference pattern within a small-volume phantom device generated using the elements of the sensor module illustrated in FIG. 9A and FIG. 9B, including an interference pattern with one sensor inactivated (Tx1) and with both sensors inactivated (Tx2);

FIG. 10D is a graph showing a measured interference pattern with motion artifacts (M) within a small-volume phantom device generated using the elements of the sensor module illustrated in FIG. 9A and FIG. 9B; and FIG. 10E is a graph showing a measured interference pattern with motion artifacts (M) within a small-volume phantom device coupled to an anti-vibration base, generated using the elements of the sensor module illustrated in FIG. 9A and FIG. 9B.

DETAILED DESCRIPTION

The systems and methods described herein relate to sensing target elements in a target environment, and more specifically, to using signal interference patterns generated by interacting signals produced by an active sensor and a reference sensor. In an aspect, the active sensor is provided with a plurality of active receptors configured to detect target elements, and the reference sensor is similar in structure to the active sensor but provided with a plurality of blocked receptors that lack capacity to detect the target element.

In one aspect, a sensor system used for sensing target elements in a target environment includes a sensor module comprising the active sensor and the reference sensor, as well as a signal system configured to obtain and analyze signal interference patterns from the sensor module. In one aspect, the target environment is within a patient, the sensor module is implanted in vivo, and the signal system is positioned ex vivo.

In some embodiments, the active and reference sensors are formed from the same type of sensor and are each further configured separately to detect target elements and to remain inert to the target elements, respectively. In an aspect, the signal system includes a transducer communicatively coupled to a controller. The controller operates the transducer to generate and direct an acoustic signal to the sensor module. The active and reference sensor of the sensor module receive the acoustic signal generated by the transducer and produce corresponding response signals. In various aspects, the response signals produced by both the active and reference sensor of the sensor module vary at least partially as a function of the mass of each sensor. In another aspect, the response signal produced by the active sensor further varies at least partially as a function of the concentration of immobilized or otherwise detected target elements. In an aspect, the response signal produced by the reference sensor does not vary in the presence of target elements within the target environment, and serve as a baseline relative to the target element-dependent response signal produced by the active sensor.

In various aspects, the response signals produced by the reference sensor and by the active sensor interact within the target environment to form signal interference patterns indicative of a presence and/or a concentration of target elements. In an aspect, the transducer of the sensor system detects the signal interference patter and controller evaluates the detected signal interference pattern to detect the presence and/or concentration of target elements. In one embodiment, the controller analyzes the detected signal interference pattern to detect the target elements.

Figure 1:
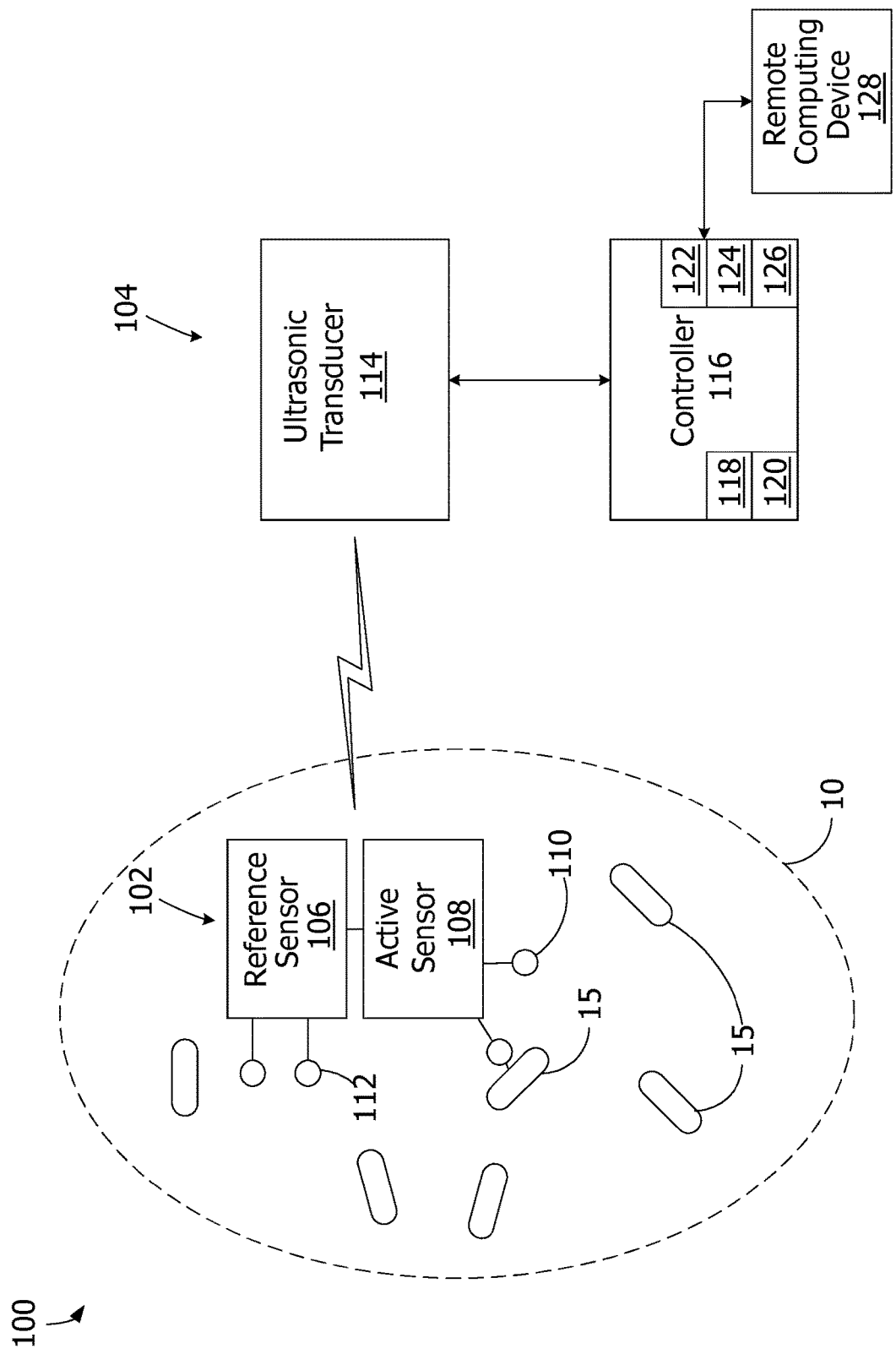
FIG. 1 is a block diagram showing a sensor system for detecting target elements in a target environment in accordance with an aspect of the disclosure.

FIG. 1 is a block diagram of a sensor system 100 for detecting target elements in a target environment in one aspect. System 100 includes a sensor module 102 that includes a reference sensor 106 and an active sensor 108, and further includes a signal system 104. In various aspects, sensor module 102 is configured to be embedded or implanted into a target environment 10 containing one or more target elements 15. In various other aspects, system 100 may include additional, fewer, or alternative components, including, but not limited to, those described elsewhere herein.

In various aspects, target environment 10 includes, but is not limited to, any suitable environment in which acoustic signals produced by signal system 104 and sensor module 102 can propagate, and in which target elements 15 are mobile and free to interact with sensor module 102. By way of non-limiting example, target environment 10 is a region or organ within a patient's body. By way of another non-limiting example, target environment 10 is a milk carton undergoing transport to a retail or distribution facility.

In various aspects, sensor module 102, when embedded, is configured to detect target elements 15 within target environment 10. Target elements 15 include, but are not limited to, any suitable bodies, molecules, and the like that sensor module 102 is configured to detect within target environment 10. Non-limiting examples of suitable target elements 15 include proteins, particulates, nanoparticles, organic and inorganic chemical compounds, and any other suitable target element 15.

In some aspects, sensor module 102 includes a reference sensor 106 and an active sensor 108. In other aspects, sensor module 102 may include a different arrangement of multiple sensors, including, but not limited to, three sensors, four sensors, or more. In at least some aspects, reference sensor 106 and active sensor 108 are the same type of sensor, as characterized by being formed from the same or similar materials and/or are configurable to collect the same type of sensor data. Alternatively, reference sensor 106 and active sensor 108 may be different types of suitable sensors that function as described herein.

In some aspects, the reference sensor 106 and active sensor 108 are passive sensors that do not require an active power source to collect sensor data as described herein. In other aspects, reference sensor 106 and active sensor 108 may be provided as low power sensors configured to operate over extended periods of time using a limited amount of power. In one aspect, reference sensor 106 and active sensor 108 are configured to harvest energy from signal system 104 to communicate as described herein. By way of non-limiting example, reference sensor 106 and active sensor 108 include piezoelectric crystals (not shown in FIG. 1) configured to absorb energy from an acoustic signal produced by signal system 104 and to generate acoustic response signal in response. In various aspects, the acoustic response signals produced by reference sensor 106 and active sensor 108 vary at least partially as a function of the resonance characteristics of reference sensor 106 and active sensor 108. Without being limited to any particular theory, the resonance characteristics of a typical body, including reference sensor 106 and active sensor 108 are proportional to the mass of the typical body. Consequently, the response signals produced by reference sensor 106 and active sensor 108 vary at least partially as a function of mass and/or other empirical measurements of reference sensor 106 and active sensor 108.

In various aspects, active sensor 108 is configured to detect target elements 15 within target environment 10. In some aspects, active sensor 108 includes one or more unblocked receptors 110 configured to immobilize or otherwise detect target elements 15. Unblocked receptors 110 may be coupled to an outer surface of active sensor 108 in a manner suitable for binding, linking, and/or otherwise complexing with target elements 15. In some aspects, unblocked receptors 110 are configured to attract target elements 15 by any known means including, but not limited to, electrostatic forces, hydrophilic/hydrophobic interactions, ionic attractions, DNA/RNA complementary sequences, biorecognition, and any other suitable means.

In various aspects, active sensor 108 is positioned within target environment 10 to promote target elements 15 binding to unblocked receptors 110. By way of non-limiting example, unblocked receptors 110 are spaced apart from one another over the outer surface of active sensor 108. By way of another non-limiting example, the outer surface of active sensor 108 is an unblocked receptor 110. In some aspects, unblocked receptors 110 are configured to detect target elements 15 without binding to target elements 15. When active sensor 108 generates a response signal for signal system 104, the response signal is at least partially a function of the total mass of active sensor 108 and the concentration of immobilized or otherwise detected target elements 15. In other aspects, the response signal is independent of mass, but instead varies as a function of one or more additional empirical measurements associated with active sensor 108.

Unlike active sensor 108, reference sensor 106 is configured to produce response signals within target environment 10 without immobilizing and/or otherwise detecting target elements 15. In various aspects, reference sensor 106 includes one or more blocked receptors 112 comparable to unblocked receptors 110, except that blocked receptors 112 are configured to be relatively inert with respect to immobilizing and/or otherwise interacting with target elements 15 within target environment 10. In one aspect, blocked receptors 112 may be the same or similar to unblocked receptors 110, but are configured to not detect target elements 15. In some aspects, unblocked receptors 110 are provided in the form of blocked receptors 112 that are further functionalized to enable detection of target elements 15. In other aspects, blocked receptors 112 are provided in the form of unblocked receptors 110 that are further modified by any suitable means including, but not limited to, an additional coating or outer layer configured to block and/or otherwise disrupt the immobilization or other detection of target elements 15 by blocked receptors 112. In various other aspects, blocked receptors 112 and/or unblocked receptors 110 are omitted from reference sensor 106, eliminating any means of immobilizing and/or otherwise detecting target elements 15.

In various aspects, reference sensor 106 may be configured to produce a response signal characterized by a frequency that is matched to a corresponding active sensor 108 in the absence of target elements 15 within target environment 10. Without being limited to any particular theory, the interference patterns resulting from the superposition of response signals generated by reference sensor 106 and active sensor 108 are enhanced when the acoustic waves of all response signals are coherent waves, defined herein as waves having the same or nearly the same frequency. In some aspects, reference sensor 106 and active sensor 108 are constructed from matching materials, except for those features that modify unblocked receptors 110 to form blocked receptors 112 or vice versa, to ensure that the response signals produced by reference sensor 106 and active sensor 108 are at least approximately coherent. In other aspects, the reference sensor 106 and active sensor 108 are constructed from different materials, but the response characteristics of the reference sensor 106 and active sensor 108 are tuned so that the response signals produced by reference sensor 106 and active sensor 108 are at least approximately coherent.

In one aspect, reference sensor 106 is configured to generate a response signal that serves as a baseline for the response signal generated by active sensor 108. In some aspects, reference sensor 106 is coupled to active sensor 108 to limit variations in the response signals of reference sensor 106 and active sensor 108 other than the variations caused by the detected target elements 15. In other aspects, reference sensor 106 is provided as a separate element from active sensor 108, and reference sensor 106 is positioned proximate to active sensor 108. Alternatively, reference sensor 106 is provided as a separate element that is positioned in target environment 10 without regard to a corresponding position or separation distance of active sensor 108.

In one aspect, signal system 104 includes a transducer 114 configured to communicate with sensor module 102 and a controller 116 configured to operate transducer 114 and analyze response signals from sensor module 102. In one aspect, target environment 10 is positioned within a patient, and signal system 104 is positioned ex vivo and communicates with implanted sensor module 102 wirelessly. In one aspect, transducer 114 is an ultrasonic transducer that generates and directs ultrasonic signals to sensor module 102. In another aspects, transducer 114 includes or is electrically connected to a power supply, a signal generator, and/or other circuitry (each not shown) that enables transducer 114 to operate as described herein. In various aspects, transducer 114 may be any suitable ultrasonic transducer that generates ultrasonic signals and receives response signals, including, but not limited to, those ultrasonic transducer included in commercially available ultrasonic imaging systems. In various other aspects, transducer 114 is be configured to generate signals having a wavelength other than ultrasonic wavelengths, including, but not limited to, radio wavelengths.

In one aspect, ultrasonic transducer 114 is positioned to direct ultrasonic signals into target environment 10, and in particular, to sensor module 102. Reference sensor 106 and active sensor 108 are each configured to absorb energy from the ultrasonic signals produced by ultrasonic transducer 114 and to subsequently generate response signals. In another aspect, ultrasonic transducer 114 is further configured to receive the response signals produced by reference sensor 106 and active sensor 108, and to transmit the received response signals to controller 116 for analysis.

In various aspects, controller 116 is configured to operate transducer 114 and to analyze response signals received by transducer 114 from sensor module 102 to identify a presence and/or concentration of target elements 15. More specifically, controller 116 controls activation of transducer 114 to generate the ultrasonic signals. In another aspect, controller 116 is further configured to analyze the response signals received from active sensor 108 and/or reference sensor 106 to determine the presence and/or concentration of any target elements 15 detected by sensor module 102. In some aspects, target elements 15 immobilized and/or otherwise detected by active sensor 108 cause at least one or more characteristics of the response signals produced by the active sensor 108 to change relative to the corresponding characteristics of the baseline response signals produced by reference sensor 106. Non-limiting examples of response signal characteristics that may change in response to immobilization or other detection of target elements 15 by active sensor 108 include an amplitude change, a frequency shift, and/or a phase shift. By analyzing one or more differences between the characteristics of the response signals produced by reference sensor 106 and by active sensor 108, controller 116 is configured to identify one or more detection parameters related to target elements 15, including, but not limited to, detection of target elements 15 by active sensor 108, an amount or concentration of target elements 15 detected by active sensor 108, and/or additional characteristics of detected target elements 15.

In one aspect, controller 116 is configured to use acoustic interferometry to identify the presence and/or concentration of target elements 15 within the target environment 10 based on the detected response signals. In this aspect, the response signals from reference sensor 106 and active sensor 108 superimpose and/or otherwise interact to generate the signal interference analyzed by controller 116. In one aspect, signal interference obtained in the presence of target elements 15 is compared to a baseline signal interference corresponding to the absence of target elements 15 to identify the presence and/or concentration of target elements 15 within the target environment 10. Without being limited to any particular theory, the analysis of signal interference associated with the interaction of response signals produced by reference sensor 106 and active sensor 108 may provide increased signal resolution for the detection of changes caused by the presence of target elements 15, relative to the corresponding signal resolution associated with analysis of changes in response signals produced by active sensor 108 in isolation.

In various additional aspects, controller 116 further includes one or more processors 118, a memory device 120, a communication interface 122, an input interface 124, and an output interface 126. In other additional aspects, controller 116 includes additional, fewer, or alternative components, including those described elsewhere herein.

In one aspect, processor 118 is communicatively coupled to memory device 120, communication interface 122, input interface 124, and/or output interface 126. Processor 118 is configured to read computer-executable instructions and perform functions based on the instructions, including functions that cause other components of controller 116 to operate. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In various aspects, memory device 120 includes one or more devices that enable information including, but not limited to, computer-executable instructions and/or other data, to be stored and retrieved. In other aspects, processor 118 is configured to retrieve instructions from memory device 120 and store data on memory device 120. In additional aspects, memory device 120 includes one or more computer readable media including, but not limited to, dynamic random access memory (DRAM), static random access memory (SRAM), a solid state disk, and/or a hard disk. In various additional aspects, memory device 120 stores application source code, application object code, configuration data, additional input events, application states, signal analysis results, signal data, and/or any other type of data without limitation.

In one aspect, communication interface 122 is configured to facilitate data communication between controller 116 and other devices. In some aspects, controller 116 is communicatively coupled to ultrasonic transducer 114 via communication interface 122. In an additional aspect, communication interface 122 is communicatively coupled with a remote computing device 128. In various aspects, remote computing device 128 is configured to operate signal system 104 and/or receive data from controller 116 for analysis.

Input interface 124 is configured to receive user input from a user to operate transducer 114 or controller 116 in various aspects. In some aspects, the user input is used to navigate through and/or manipulate data collected and/or generated by controller 116. Non-limiting examples of input interface 124 include a keyboard, a pointing device, a mouse, a stylus, a touch sensitive panel (e.g., a touch pad, a touch screen), a gyroscope, an accelerometer, a position detector, and/or an audio input interface (e.g., including a microphone).

Output interface 126 is configured to present information, such as analysis of the response signals from sensor module 102, to the user in various aspects. Non-limiting examples of output interface 126 include a visual display device, such as a cathode ray tube (CRT), a liquid crystal display (LCD), an organic LED (OLED) display, and/or an "electronic ink" display. Other and/or additional non-limiting examples of output interface 126 include an audio output device (e.g., an audio adapter and/or a speaker) and/or a printer. In some aspects, controller 116 does not include input interface 124 and/or output interface 126. In one aspect, remote computing device 128 is configured to receive user input and/or present information to the user.

Figure 2:
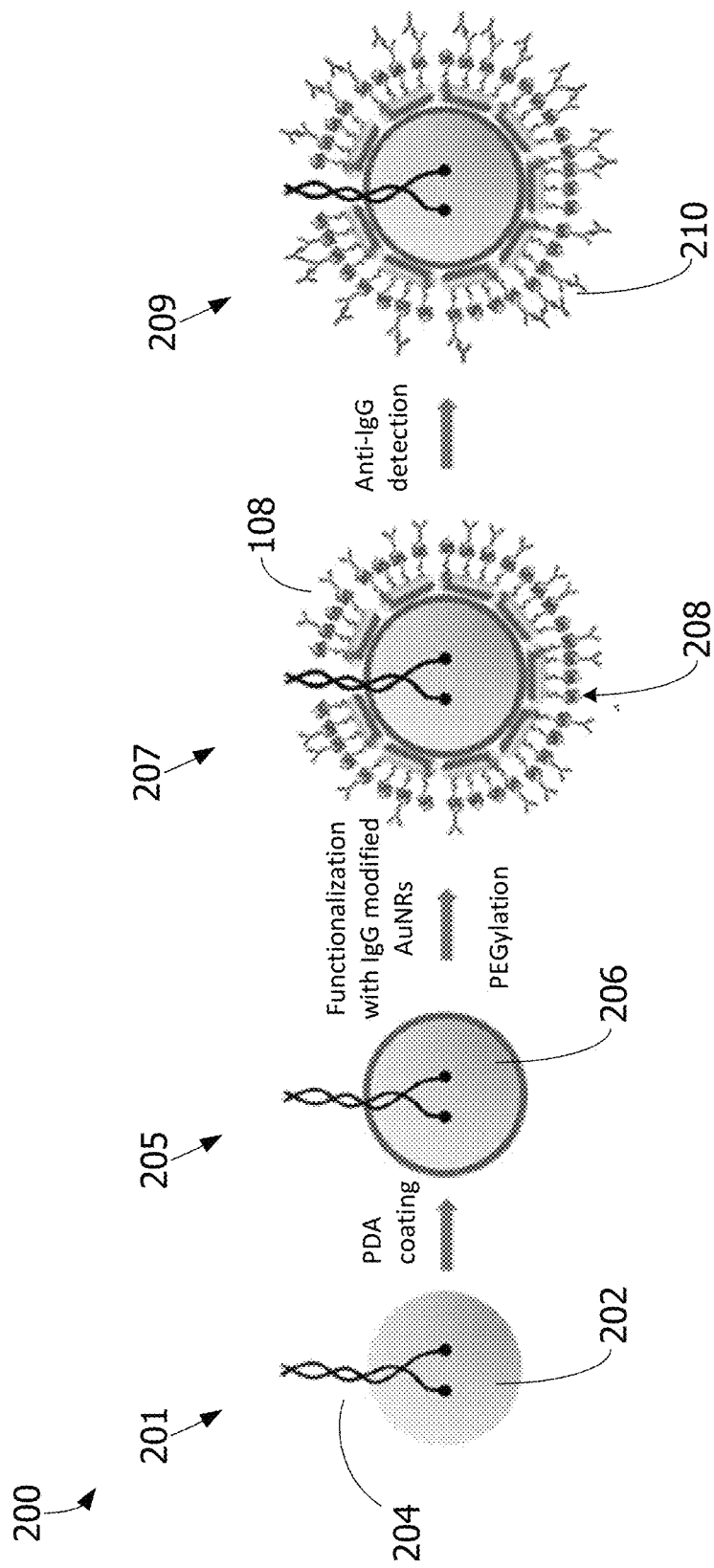
FIG. 2 is a schematic diagram illustrating intermediate steps in the formation and functionalization of a representative active sensor in accordance with an aspect of the disclosure.

FIG. 2 is a schematic diagram illustrating various intermediate products associated with the fabrication process 200 used to produce an active sensor 108 for use with system 100 (shown in FIG. 1). More specifically, the diagram depicts a process 200 for configuring active sensor 108 to detect target elements 210.

As illustrated in FIG. 2, at a first stage 201, a sensor body 202 and wires 204 are coupled together. In one aspect, body 202 is a piezoelectric crystal that absorbs energy from wireless signals and generates a response signal and/or generates a signal in response to power delivered by wires 204 from a power source (not shown). By way of non-limiting example, piezoelectric crystal is formed from a PZT-5H piezoceramic material. In some aspects, wires 204 are electrically conductive wires that retrieve electrical energy or provide electrical energy to sensor body 202. In some aspects, wires 204 are connected to an electrical system or circuit (not shown) configured to facilitate data communication and/or other functions. In other aspects, wires 204 are connected to an electrical system or circuit (not shown) configured to harvest energy from the ultrasonic signal and/or to drive active sensor 108 at a resonant frequency to generate the response signal. In other additional aspects, wires 204 are not electrically conductive and are configured to facilitate movement and positioning of active sensor 108. Although two wires 204 are illustrated in FIG. 2, in various aspects active sensor 108 includes any suitable number of wires 204 to function as described herein including, but not limited to one wire or no wires.

Referring again to FIG. 2, at a second stage 205, a coating 206 is applied to sensor body 202. Coating 206 is configured to protect sensor body 202 from target environment 10, thereby increasing the effective usable life of active sensor 108. Coating 206 may also prevent ultrasonic waves near resonant frequencies from propagating through target environment 10. Non-limiting examples of suitable coatings 206 include a polytetrafluoroethylene (TEFLON®) coating and a polydopamine (PDA) coating. In additional aspects, coating 206 is selected for active sensor 108 based upon an intended target environment.

At a third stage 207 of process 200, active sensor 108 is functionalized with a receptor layer 208 that is configured to immobilize and/or otherwise detect target element 210. In various aspects, the receptor layer 208 includes at least one chemical moiety configured to immobilize and/or otherwise detect target elements 15. In various additional aspects, receptor layer further includes labeling moieties configured to enhance the quality of the response signal produced by the active sensor 108. By way of non-limiting example, active sensor 108 is functionalized with IgG configured to immobilize anti-immunoglobulin 210 (anti-IgG). More specifically, active sensor 108 is functionalized using a receptor layer 208 containing gold-nanoparticle (AuNR) labeled immunoglobulin (IgG) in this example. In various aspects, a reference sensor 106 is formed using stages 201, 205, and 207 of process 200 as illustrated in FIG. 2, followed by an additional stage of PEGylation of the receptor layer 208 to block the receptors and preventing target elements 15 (i.e. anti-IgG 210) from binding to anti-IgG 210.

Referring again to FIG. 2, the IgG probes are configured to immobilize anti-IgG target elements 210 at a fourth stage 209. In particular, hybridization occurs between the IgG probes and anti-IgG target elements 210. When an ultrasonic signal is received by active sensor 108, any anti-IgG target elements 210 immobilized on active sensor 108 modifies the resonance characteristics of active sensor 108. In particular, immobilized anti-IgG target elements 210 cause a frequency shift in the harmonics of the response signals produced by active sensor 108.

Figure 3:
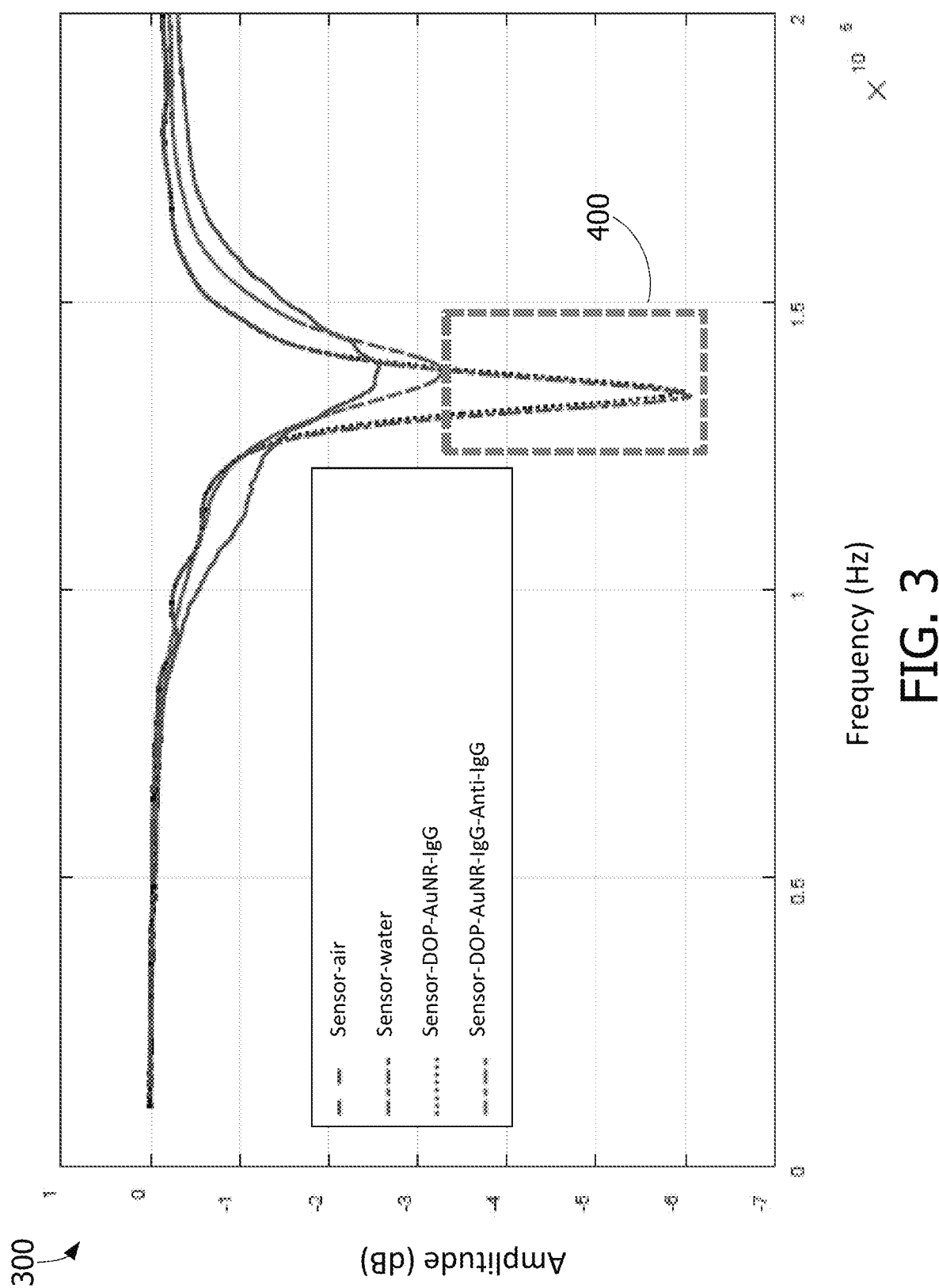
FIG. 3 is a graph comparing response signals from an active sensor with and without immobilized target elements.

FIG. 3 is graph 300 summarizing the response signals produced by the active sensor 108 and intermediate sensors produced at different stages of the process 200 illustrated in FIG. 2. Graph 300 compares the frequency responses and resonant frequencies produced by the non-functionalized sensor 206 illustrated in FIG. 2 in air (labeled "sensor-air" in FIG. 3) and in water (labeled "sensor-water" in FIG. 3). In addition, graph 300 compares the frequency responses and resonant frequencies produced by the functionalized active sensor 108 illustrated in FIG. 2 in water with no immobilized IgG (labeled "Sensor-DOP-AuNR-IgG" in FIG. 3). Further, graph 300 compares the frequency responses and resonant frequencies produced by the functionalized active sensor 108 illustrated in FIG. 2 with immobilized IgG (labeled "Sensor-DOP-AuNR-IgG-Anti-IgG" in FIG. 3) induced by exposure to solution with an anti-IgG concentration of 15 µg/mL.

As shown in graph 300, the non-functionalized sensor (see "Sensor-water" in FIG. 3) produced response signals at a resonant frequency of about 1.4 megahertz (MHz) that shifted to a lower resonant frequency with the addition of the receptor layer (see "Sensor-DOP-AuNR-IgG" in FIG. 3). In addition to the shift in resonant frequency, the quality factor of the resonance also increased after functionalization, as evidenced by the deeper, narrower peak of the "Sensor-DOP-AuNR-IgG" response signal relative to the "Sensor-water" response signal as illustrated in FIG. 3. This increase in quality factor is unlike what is observed in biosensors based on quartz crystal microbalance (QCM) or surface acoustic wave (SAW). Without being limited to any particular theory, the increase of the quality factor may be attributed to an acoustic impedance mismatch created by the formation of the PDA coating which prevents ultrasonic waves (of different frequencies around the resonant frequency) to propagate into the surrounding tissue. In various aspects, the increase in the quality factor enables detection and/or measurement of acute resonance frequency shifts due to the hybridization events (i.e., the binding of the anti-IgG to the IgG of the sensor).

Figure 4:
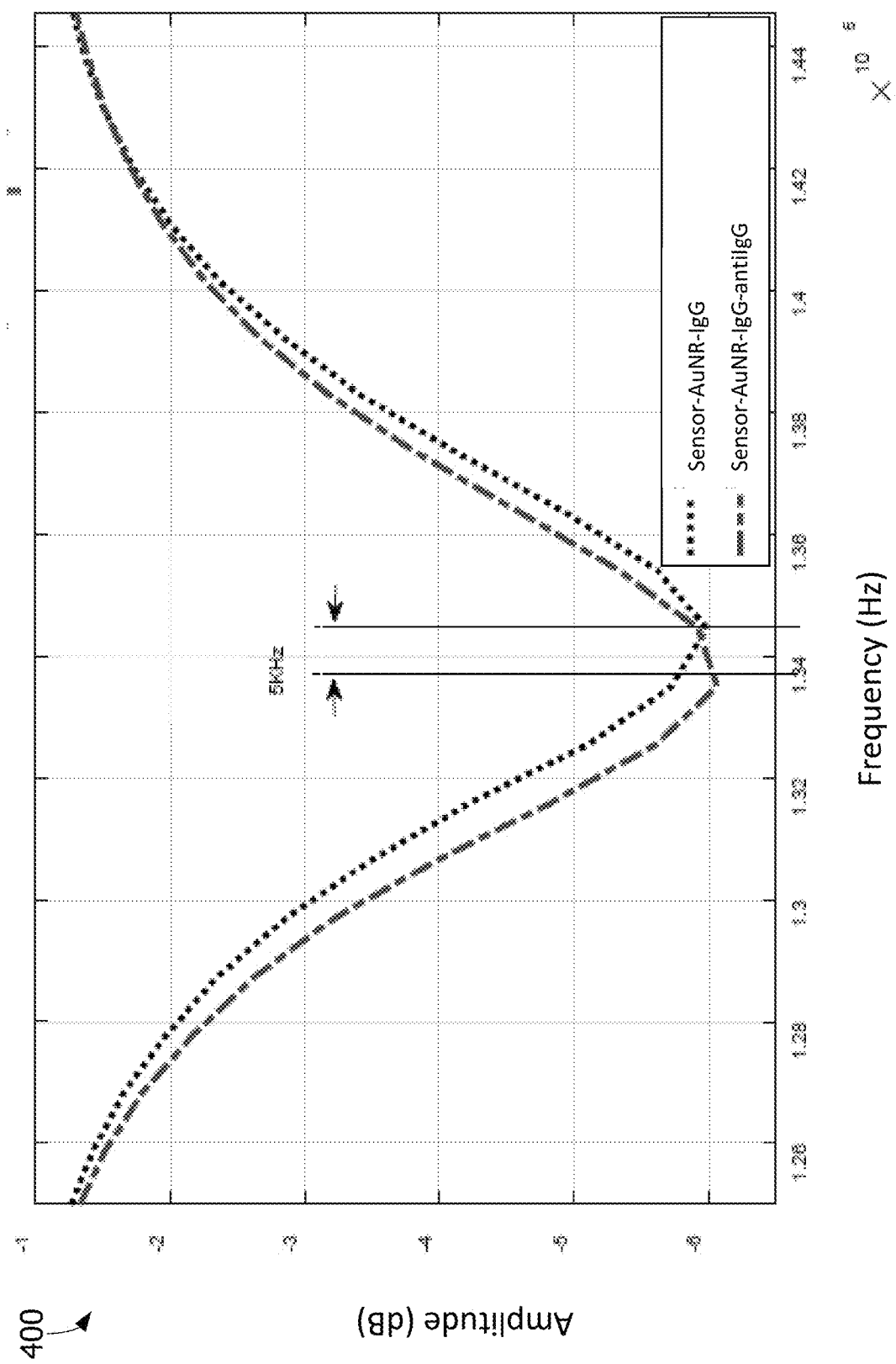
FIG. 4 is an enlargement of a portion of FIG. 3, demarcated by an overlaid rectangle.

FIG. 4 is an enlarged portion of graph 300 from FIG. 3 defined by box 400 shown in FIG. 3 highlighting the frequency shift between a functionalized sensor with immobilized anti-IgG target elements (red line, "Sensor-DOP-AuNR-IgG-Anti-IgG") and a functionalized sensor that is not bound to anti-IgG target elements (black line, "Sensor-DOP-AuNR-IgG"). AS illustrated in graph 400 of FIG. 4, the immobilized anti-IgG target elements induced a 5 kilohertz frequency shift in the resonance characteristics of the response signal. This frequency shift at least depends on the mass of the sensor and any immobilized anti-IgG target elements.

To increase the quality factor and resolution of frequency shifts, a reference sensor is introduced with the active sensor to enable the use of acoustic interferometric techniques. FIG. 5A is a schematic diagram 500 illustrating elements forming interference patterns associated with the acoustic interferometric techniques including, but not limited to, a transducer 114, reference sensor 106 and active sensor 108 (each shown in FIG. 1). FIG. 5B shows a representative interference pattern 501 detected by transducer 114 using the disclosed acoustic interferometric techniques. As illustrated in FIG. 5A, transducer 114 generates an ultrasonic signal 502 directed towards reference sensor 106 and active sensor 108. Ultrasonic signal 502 includes a series of periodic acoustic pulses, each acoustic pulse containing at least one acoustic wave with an ultrasonic wavelength. Ultrasonic signal 502 is received by reference sensor 106 and active sensor 108, and reference sensor 106 and active sensor 108 both generate reference response signals 504 and active response signals 506, respectively. The frequencies of reference response signals 504 and active response signals 506 depend at least in part on the resonant characteristics (i.e., harmonic frequencies) of the reference sensor 106 and active sensor 108. Without being limited to any particular theory, the resonant characteristics depend at least partially upon the total mass of reference sensor 106 and active sensor 108 and, for active sensor 108, any bound target elements 15. Reference response signals 504 and active response signals 506 interact to form an interference pattern 501 that is detected by transducer 114 in the form of a total response signal 508. Total response signal 508 represents any response signals (including reference response signal 504 and active response signal 506) from sensors and may include other signals generated within the target environment in response to ultrasonic signal 502.

Transducer 114 and/or controller 116 (shown in FIG. 1) are configured to filter and/or process total response signal 508 to remove noise from signal 508. Signal 508 is indicative of signal interference between reference response signals 504 and active response signals 506, and after processing, the total response signal 508 is displayed as interference pattern 501, shown illustrated in FIG. 5B. If a frequency shift of the signal interference occurs due to immobilization of target elements 15 to active sensor 108, interference pattern 501 is modified. Controller 116 is configured to extract data associated with the signal interference, including, but not limited to, a resonant frequency of the signal interference, from interference pattern 501 using any suitable signal processing techniques without limitation. In certain embodiments, controller 116 extracts reference response signal 504 from total response signal 508 to determine a baseline resonant frequency for comparison with the resonant frequency of the signal interference. In other embodiments, controller 116 stores interference pattern 501 for reference sensor 106 and active sensor 108 without any bound target elements for comparison with subsequently-received signal interference to detect changes in interference pattern 501 associated with the immobilization of target elements 15 on the active sensor 108. In various aspects, this change in interferometric frequency compared to the baseline resonant frequency is greater than the change in resonant frequency of active sensor 108 compared to the baseline resonant frequency (see FIG. 4). By way of non-limiting example, the change in interferometric frequency due to immobilization of target elements 15 on the active sensor 108 is approximately a thousand times larger than the relative change of the resonant frequency of active sensor 108.

Figures 6A, 6B:
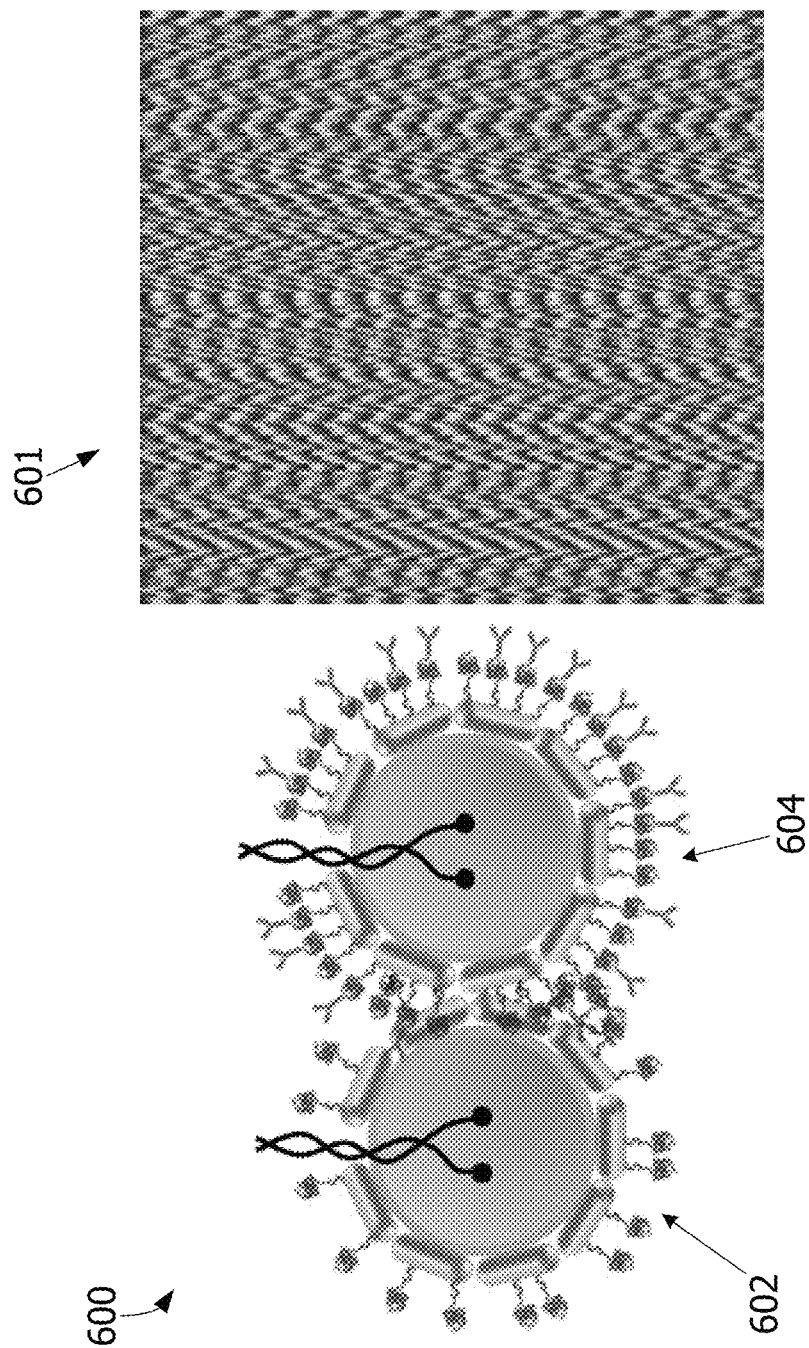
FIG. 6A is a schematic diagram showing a reference sensor and an active sensor of a sensor module in accordance with an aspect of the disclosure.
FIG. 6B is a graph showing a measured signal interference pattern generated using the sensor module illustrated in FIG. 6A.

By way of non-limiting example, the acoustic interferometric techniques were used to detect anti-IgG target elements. FIG. 6A is a diagram showing a sensor module 600 that includes a reference sensor 602 and an active sensor 604 arranged in close proximity to limit variations in the response signals induced by effects other than the variations caused by the detection of target elements. The active sensor 604 was an ultrasonic crystal functionalized with gold-nanoparticle (AuNR) labeled immunoglobulin (IgG) formed using a process similar to process 200 illustrated in FIG. 2 and described above. The reference sensor 602 was formed in a similar manner to the active sensor 604 and was further PEGylated to prevent immobilization of anti-IgG to the reference sensor 602. A COTS ultrasound imager (100 MHz sampling rate, 16-bit resolution) was used to detect the signal interference of response signals produced by the activated reference sensor 602 and activated active sensor 604. FIG. 6B shows the corresponding interference pattern 601 obtained before exposure of the sensor module 600 to anti-IgG target elements.

Figure 8:
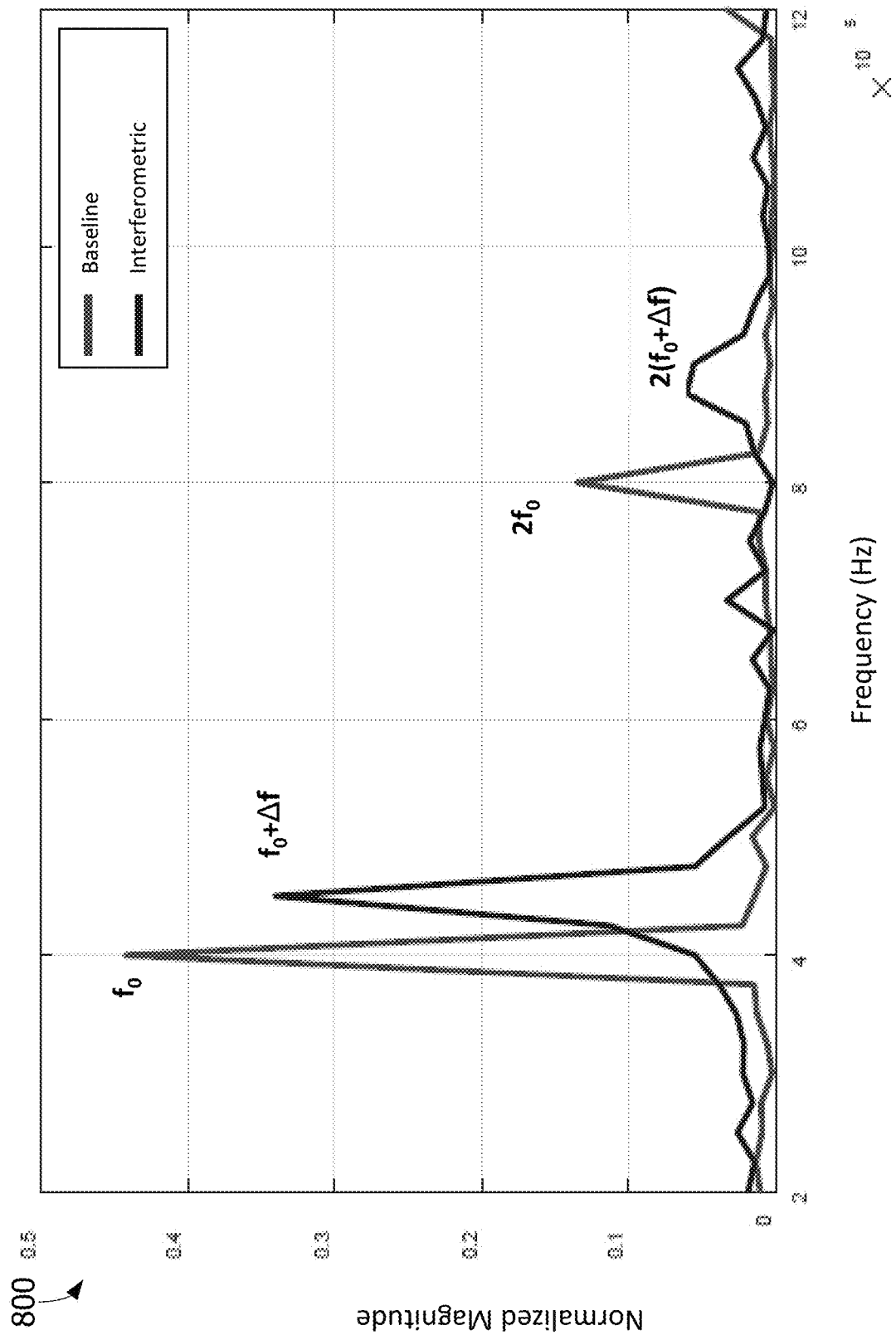
FIG. 8 is a graph comparing resonant frequencies of the sensor modules shown in FIG. 6 (baseline sensor module) and in FIG. 7 (sensor module with immobilized target elements)

In this example, sensor module 600 was then exposed to anti-IgG in solution at a concentration of 15 µg/mL. FIG. 7 is a diagram of sensor module 600 after exposure to the anti-IgG target elements 702, shown immobilized on active sensor 604. FIG. 7B shows the corresponding interference pattern 701 obtained after exposure of the sensor module 600 to the anti-IgG target elements. FIG. 8 is a graph 800 comparing the frequency responses and resonance frequencies obtained by analysis of the interference patterns 601, 701.

After hybridization of the anti-IgG target elements (concentration level of 15 µg/mL) on the active sensor 604, the interference pattern changed from pattern 601 to pattern 701. Both the patterns 601, 701 were post-processed (e.g., by controller 116, shown in FIG. 1) to determine the shift in interference frequencies. Compared to a baseline resonant frequency, the resulting shift in interference frequency was 30% compared to a frequency shift of 0.3% when using active sensor 604 without reference sensor 602.

In various aspects, the increased resolution of the interference frequency shift enables the detection of ng/mL changes in the concentration levels of target elements. In additional aspects, improvements to the frequency shift resolution may be obtained by analyzing second or third order harmonics of the interference patterns as shown in graph 800 of FIG. 8 in addition to, or in lieu of, the first order harmonics. Although second or third order harmonics increase the processing requirements to detect the frequency shifts, sensor module 600 delegates the computationally intensive image processing and post-processing to the ultrasound imager, which is configured to satisfy these requirements. In some aspects, the ultrasound imagers for use in system 100 (i.e., as signal system 104) are configured to generate real-time, high-resolution images at rates exceeding seven thousand frames per second. In other aspects, the ultrasound imagers are also portable or hand-held to facilitate imaging in non-clinical environments.

EXAMPLES

The following example illustrates various aspects of the disclosure.

Example 1: Sensitivity and Stability of Acoustic Interferometry of Functionalized Piezoelectric Crystals To assess the sensitivity and stability of the acoustic interferometric technique described above to variation in the target environment, the following experiments were conducted.

Figure 9A:
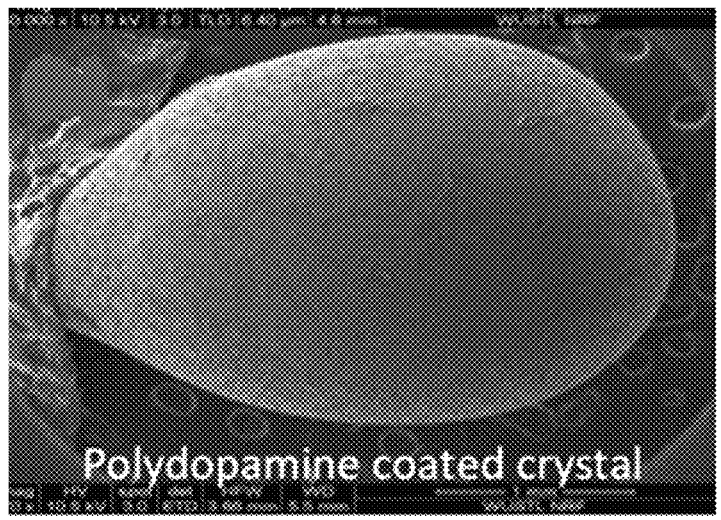
FIG. 9A is a scanning electron microscope image showing a reference sensor of a sensor module that includes a crystal surface coated with polydopamine.
Figure 9B:
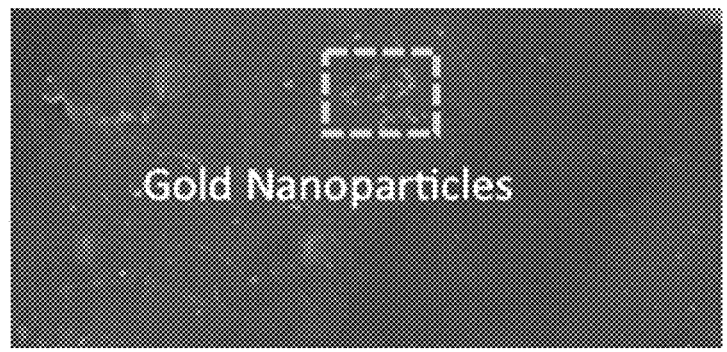
FIG. 9B is a scanning electron microscope image showing an active sensor of a sensor module formed by immobilizing gold nanotubes on the surface of a sensor similar to the reference sensor illustrated in FIG. 9A.

To assess the sensitivity and stability of the acoustic interferometric technique changes in ultrasound generation and propagation properties due to immobilization of target analytes on the surface of an ultrasound crystal were measured within a variety of target environments. For these experiments, two phantoms were designed, one larger and one smaller. Each phantom included transmitter ultrasound crystals (Tx1 and Tx2) and a receiver (Rx) ultrasound crystal with a frequency of 1.3 MHz, encapsulated in Teflon and fixated inside a plexiglass interferometry chamber. The surfaces of both transmitter crystals were modified using a polydopamine layer, as shown in FIG. 9A, and to emulate immobilization of target analytes on the surface of the transmitter crystal functioning as an active sensor, gold-nanoparticles were immobilized on the polydopamine layer of one transmitter crystal, as shown in FIG. 9B. One objective was to detect and quantify the amount of gold nanoparticles captured on the surface of the active sensor. Interference lines are generated using an ultrasound echoscope operating in a pulse-echo mode.

Measured interference lines obtained for various target environments are shown in FIGS. 10A, 10B, 10C, 10D, and 10E. FIG. 10A shows the interference lines obtained using the larger phantom setup. Ultrasonic pulses were generated using the transmitters Tx1 or Tx2 and the reflected echoes are captured by the echoscope to form each of the interference bands (a1-a3) shown illustrated in FIG. 10A. For the larger phantom results illustrated in FIG. 10A, the interference lines in the bands were not well separated.

FIG. 10B shows the interference lines obtained using the smaller phantom setup. As illustrated in FIG. 10B, for the smaller phantom the interference lines b1 and b2 were well.

For the rest of the experiments the smaller phantom was used to obtain interferometric measurements. FIG. 10C shows interference lines obtained by activating individual crystals (shown in region Tx1) or multiple crystals (shown in region Tx2). As illustrated in FIG. 10C, the interference patterns were influenced by the activation of individual or multiple crystals.

FIG. 10D shows interference lines obtained using the smaller phantom setup with the effects of motion of the phantom shown in region M. As shown in FIG. 10D, the interferometric technique has high sensitivity to motion. In addition, the system did not recover back the original interference pattern after the motion had ceased, as illustrated by changes in interference line d1 in FIG. 10D. FIG. 10E shows interference lines obtained using the smaller phantom setup that included an anti-vibration base, with the effects of motion of the phantom shown in region M. The motion-induced effects within region M of FIG. 10E were reduced by the use of an anti-vibration base, as shown by the less severe changes of interference line e1.

The results of these experiments demonstrated the sensitivity and stability of the disclosed acoustic interferometric technique with functionalized ultrasound sensors.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor system for detecting target elements in an environment, the sensor system comprising:
    a sensor module comprising an active sensor and a reference sensor, each of the active sensor and the reference sensor comprising a sensor body having a coated surface, the active sensor further comprising an unblocked receptor layer applied over the coated surface, and the reference sensor further comprising a blocked receptor layer applied over the coated surface, wherein:
        the active sensor is configured to immobilize the target elements on the unblocked receptor layer and to generate a response signal proportional to a concentration of the immobilized target elements in response to an ultrasonic signal; and
        the reference sensor is inert to the target elements and is configured to generate a reference signal in response to the ultrasonic signal; and
    a signal system comprising an ultrasonic transducer communicatively coupled to a controller, wherein:
        the ultrasonic transducer is configured to generate the ultrasonic signal and to receive a signal interference comprising a superposition of the response signal and the reference signal; and
        the controller is configured to transform the signal interference to detect the concentration of the target elements.

2. The sensor system of claim 1, wherein the sensor body comprises a piezoelectric body configured to absorb energy from the ultrasonic signal and to generate a response signal or a reference signal at a resonant frequency.

3. The sensor system of claim 2, wherein the resonant frequency of the response signal shifts at least partially as a function of the concentration of the target elements immobilized to the unblocked receptor layer.

4. The sensor system of claim 1, wherein the sensor module is configured to be implanted in vivo to detect the target elements within a patient and the signal system is positioned ex vivo.

5. The sensor system of claim 1, wherein the active sensor is coupled to the reference sensor.

6. A method for detecting target elements within an environment, the method comprising:
    positioning a sensor module within the environment, the sensor module comprising an active sensor and a reference sensor, each of the active sensor and the reference sensor comprising a sensor body having a coated surface, the active sensor further comprising an unblocked receptor layer applied over the coated surface and the reference sensor further comprising a blocked receptor layer applied over the coated surface;
    producing and directing an ultrasonic signal to the sensor module using an ultrasonic transducer;
    receiving, at the ultrasonic transducer, a signal interference comprising a superposition of a response signal produced by the active sensor and a reference signal produced by the reference sensor in response to the ultrasonic signal, wherein the response signal is proportional to a concentration of the target elements immobilized to the unblocked receptor layer of the active sensor; and
    transforming, using a controller communicatively coupled to the ultrasonic transducer, the signal interference into a detected concentration of the target elements.

7. The method of claim 6, wherein producing and directing the ultrasonic signal to the sensor module using the ultrasonic transducer further comprises directing the ultrasonic signal such that the response signal and the reference signal are generated at substantially the same time.

8. The method of claim 6, further comprising immobilizing the target elements to the unblocked receptor layer of the active sensor, wherein the unblocked receptor layer comprises a plurality of unblocked receptors, each unblocked receptor configured to immobilize one of the target elements.

9. The method of claim 6, wherein the sensor body comprises a piezoelectric body configured to absorb energy from the ultrasonic signal and to generate a response signal or a reference signal at a resonant frequency.

10. The method of claim 9, wherein the resonant frequency of the response signal shifts at least partially as a function of the concentration of the target elements immobilized to the unblocked receptor layer.

11. The method of claim 6, wherein transforming the signal interference into a detected concentration of the target elements comprises comparing the signal interference to a reference signal interference obtained in the absence of target elements.

12. The method of claim 6, wherein positioning the sensor module in the environment further comprises positioning the sensor module in vivo within a patient and positioning the ultrasonic transducer ex vivo and acoustically coupled to the sensor module.

13. The method of claim 12, wherein positioning the sensor module in vivo further comprises positioning the active sensor adjacent the reference sensor within the environment.

14. The method of claim 6, wherein positioning the sensor module within the environment further comprises coupling the active sensor to the reference sensor.

15. A sensor module for detecting target elements in an environment, the sensor module comprising:
    an active sensor and a reference sensor, each of the active sensor and the reference sensor comprising a sensor body having a coated surface, the active sensor further comprising an unblocked receptor layer applied over the coated surface and the reference sensor further comprising a blocked receptor layer applied over the coated surface, wherein:

the active sensor is configured to immobilize the target elements on the unblocked receptor layer and to generate a response signal proportional to a concentration of the immobilized target elements in response to an ultrasonic signal;

the reference sensor is inert to the target elements and is configured to generate a reference signal in response to the ultrasonic signal; and the response signal and the reference signal are configured to superimpose to form a signal interference detectable by an ultrasonic transducer, wherein the signal interference is transformable by a controller operatively coupled to the ultrasonic transducer into a detected concentration of the target elements.

16. The sensor module of claim 15, wherein the unblocked receptor layer comprises a plurality of unblocked receptors, each unblocked receptor configured to immobilize one of the target elements.

17. The sensor module of claim 15, wherein the sensor body comprises a piezoelectric body configured to absorb energy from and to generate a response signal or a reference signal at a resonant frequency.

18. The sensor module of claim 17, wherein the resonant frequency of the response signal shifts at least partially as a function of the concentration of the target elements immobilized to the unblocked receptor layer.

19. The sensor module of claim 15, wherein the active sensor is coupled to the reference sensor.

20. The sensor module of claim 15, wherein the sensor module is configured to be implanted in vivo within a patient.

* * * * *